(12) United States Patent
Takala et al.

(10) Patent No.: US 8,715,193 B2
(45) Date of Patent: May 6, 2014

(54) DETERMINATION OF THE CLINICAL STATE OF A SUBJECT

(75) Inventors: Panu Takala, Helinski (FI); Matti Huiku, Espoo (FI)

(73) Assignee: General Electric Company, Schenectady, NY (US)

( * ) Notice: Subject to any disclaimer, the term of this patent is extended or adjusted under 35 U.S.C. 154(b) by 2595 days.

(21) Appl. No.: 11/089,528

(22) Filed: Mar. 24, 2005

(65) Prior Publication Data

US 2006/0217614 A1 Sep. 28, 2006

(51) Int. Cl.
*A61B 5/02* (2006.01)
*A61B 5/08* (2006.01)

(52) U.S. Cl.
USPC .......................................... 600/481; 600/484

(58) Field of Classification Search
USPC .................. 600/481, 483, 544, 545
See application file for complete search history.

(56) References Cited

U.S. PATENT DOCUMENTS

| | | | | |
|---|---|---|---|---|
| 5,083,571 | A * | 1/1992 | Prichep | 600/544 |
| 6,120,443 | A | 9/2000 | Cohen-Laroque | |
| 6,801,803 | B2 | 10/2004 | Viertiö-Oja | |
| 2002/0035315 | A1* | 3/2002 | Ali et al. | 600/300 |
| 2003/0055343 | A1* | 3/2003 | Korhonen | 600/481 |
| 2003/0105409 | A1* | 6/2003 | Donoghue et al. | 600/545 |
| 2004/0215263 | A1 | 10/2004 | Virag et al. | |
| 2005/0010116 | A1 | 1/2005 | Korhonen et al. | |

FOREIGN PATENT DOCUMENTS

| | | |
|---|---|---|
| EP | 0 553 162 | 5/1997 |
| EP | 1 273 265 | 1/2003 |
| EP | 1 642 525 | 4/2006 |
| FR | 2 859 911 | 3/2005 |
| WO | WO-2004/034897 | 4/2004 |

OTHER PUBLICATIONS

Palus, Milan. "Coarse-grained entropy rates for characterization of complex time series". Santa Fe Institute, Nov. 23, 1995.*
EP Communication including Search Report dated Sep. 29, 2006.
U.S. Appl. No. 11/089,548, filed Mar. 24, 2005, Huiku et al.
U.S. Appl. No. 11/089,529, filed Mar. 24, 2005, Huiku.
U.S. Appl. No. 11/954,040, filed Sep. 29, 2004, Huiku.

* cited by examiner

*Primary Examiner* — Patricia Mallari
*Assistant Examiner* — Christian Jang
(74) *Attorney, Agent, or Firm* — Andrus Intellectual Property Law, LLP (57) ABSTRACT

The invention relates to the determination of the clinical state of a subject. In order to bring about an uncomplicated method for monitoring the clinical state of a subject and for accomplishing a diagnostic scale, such as a nociception scale, on which a certain reading corresponds to the same level for all patients, a normalization transform is applied to a measurement signal containing physiological data obtained from a patient, whereby a normalized measurement signal having a predetermined value range is obtained. The normalization transform is dependent on predetermined history data, such as previous signal data of said measurement signal. A diagnostic index dependent on the normalized measurement signal is then formed, the diagnostic index serving as a measure of the clinical state of the patient. The diagnostic index may be formed based on one or more normalized measurement signals.

67 Claims, 6 Drawing Sheets

FIG. 5a — Group Average

FIG. 5b — Individual Patient Distribution

FIG. 5c — Partially Adapted Patient Distribution

FIG. 5d — Cumulative Patient Distribution

Parameter Value

DETERMINATION OF THE CLINICAL STATE OF A SUBJECT

FIELD OF THE INVENTION

The present invention relates generally to the determination of the clinical state of a subject. One application of the invention is the determination of the nociceptive or antinociceptive state of a patient.

BACKGROUND OF THE INVENTION

Pain is an unpleasant sensory or emotional experience that is associated with actual or potential tissue damaging stimuli. It is always an individual and subjective sensation, which may be acute (nociceptive), elicited by noxious stimuli, or chronic pain that has outlived its usefulness to preserve tissue integrity. The perception of pain takes mainly place at cortex, and it may be suppressed in deep sedation and anesthesia by the general (global) inhibitory effects of sedative drugs and anesthetic agents. The responses to noxious stimulus may also be suppressed when the pain signal pathway is sufficiently suppressed at the subcortical level, often in the region of the brainstem and spinal cord. Both cortical and subcortical mechanisms play a role in pain management in modern surgical anesthesia or intensive care.

Analgesia refers to absence of pain or loss of sensitivity to stimulation that would normally be painful. Analgesic state is independent of the level of consciousness of the patient.

Noxious stimuli, such as pin pricks or inflammation exceeding a certain threshold stimulus level in nociceptive nerve fibers (nociceptors), cause a nociception, i.e. a neuronal signal or perception that denotes the induced pain or injury. Nociception is transmitted in the Central Nervous System (CNS) via several different ascending pathways causing responses that can be cortical pain responses or subcortical stress responses. NSAIDs (Non-Steroidal Anti-Inflammatory Drugs) effectively relief pain at a damaged tissue site, whereas opioids selectively affect the pain pathways in the region of the spinal cord or the brainstem. Local or regional anesthetic agents, for instance those used in epidural analgesia, block both the pain and the sensory pathways in the spinal cord region.

Antinociception normally refers to the blocking or suppression of nociception in the pain pathways at the subcortical level. It may be described as subcortical analgesia, in distinction to preventing the perception of pain at the cortex, i.e. cortical analgesia.

The autonomic nervous system (ANS) is the 'unconscious' nervous system, which controls and regulates virtually all of our basic body functions, such as cardiac function, blood circulation and glandural secretion. The main parts of the ANS are the parasympathetical and sympathetical nervous branches. The sympathetical nervous system usually prepares us for high stress situations by speeding up the body functions. Under conditions of normal ANS regulation, the parasympathetical system restores the normal conditions in blood circulation by slowing down the heart rate. Pain, discomfort, and surgical stress may activate the sympathetical branch of the ANS and cause an increase in blood pressure, heart rate and adrenal secretions.

Neuromonitoring is a subfield of clinical patient monitoring focused on measuring various aspects of brain function and on changes therein caused by drugs commonly used to induce and maintain anesthesia in an operation room or sedation in patients under critical or intensive care.

Electroencephalography (EEG) is a well-established method for assessing brain activity by recording and analyzing the weak biopotential signals generated in the cortex of the brain with electrodes attached on the skin of the skull surface. The EEG has been in wide use for decades in basic research of the neural systems of the brain, as well as in clinical diagnosis of various neurophysiological diseases and disorders.

Electromyography (EMG) is a method for recording electrical biopotentials of muscles. In an EMG measurement, the electrodes are attached on the surface of the skin at a muscle group. An EMG signal is often recorded from the skull of the patient, whereby the recorded signal indicates both the activity of the facial muscle (fEMG) and the brain (EEG). As the frequencies of the EMG spectrum are usually high and above the frequencies of brain activity, the signal components can be separated by methods of signal processing or spectral analysis from the EEG signal.

Electrocardiography (ECG) is another well-established method for assessing cardiac function by recording and analyzing the biopotential signals generated in the heart. Electrodes are attached on the skin of the chest with more peripheral references. The ECG is commonly used for diagnosing cardiac dysfunctions, various cardiac and circulatory diseases, and arrhythmias. Heart rate (HR), often derived from the ECG waveform, is one of the most important parameters characterizing the condition of a patient.

Respiration rate is another vital sign, which is often monitored even in basic patient care. In connection with anesthesia and sedation of ventilated patients, monitoring of the respiration is often combined with monitoring of gas exchange, which includes monitoring of inhaled and exhaled oxygen, carbon dioxide and anesthetic gases. In modern gas monitors, airway pressure (AWP) and gas flows are also measured in order to improve the safety and quality of the ventilation.

Blood pressure (maintaining blood circulation) is yet another vital sign obtained from a patient. It may be monitored either non-invasively (NIBP) or invasively (InvBP) using catheters inserted in the arteries or veins. The latter techniques are continuous and they allow a detailed monitoring of the regulation of the cardiac-circulatory and pulmonary functions.

Pulse oximetry is a well-established technique for measuring oxygen saturation (SpO2) in arterial blood. SpO2 is an important parameter, nowadays often called as the fourth vital sign, which relates to the adequacy of oxygen supply to peripheral tissues and organs. Pulse oximeters also display a photoplethysmographic (PPG) pulse waveform, which can be related to tissue blood volume and blood flow, i.e. the blood circulation, at the site of the measurement, typically in finger or ear. The amplitude of a PPG waveform is a sensitive indicator of patient discomfort and pain, but it also reacts to non-noxious stimulations.

Analysis methods using the heart rate variability (HRV) are emerging techniques for diagnosing cardiac diseases, such as lack of oxygen supply to the cardiac muscle, and for characterizing the cardiac function and the condition of the patient in general. Fast changes in the heart rate are usually caused by the parasympathetical ANS control mediated in the vagal cranial nerve. Vagal control slows down the heart beat. The slow variations (<0.15 Hz) of the heart rate are mainly associated with sympathetical activity, which accelerates the heart beat. The ratio of the fast components of the HRV to the slow components of the HRV is often called the sympatho-vagal balance, which in emergency or during intense surgical stress turns to sympathetical dominance.

During the past few years, several commercial devices for measuring the level of consciousness and/or awareness in a clinical set-up during anesthesia have become available. These devices, which are based on a processed one-channel EEG signal, have been introduced by Aspect Medical (Bispectral Index), by Datex-Ohmeda (Entropy Index) and by Danmeter (an auditory evoked EEG potential monitoring device, AAI™). At present, the situation with the assessment of the cortical activity and integrity is considered satisfactory, though not resolved for all applications.

As to the central nervous system (CNS), the assessment or measurement of the suppression of the sub-cortical activity, the ANS and the integrity of subcortical evaluations is far more unsatisfactory. No commercial devices exist for this purpose. This is mainly because the sub-cortical components are not represented in any single bioelectrical or other signal, in contrast to that the EEG almost alone may represent the cortical activity. The monitoring of the adequacy of anesthesia or sedation thus—in addition to monitoring the hypnotic state of brains by EEG—call for a multi-parameter approach, which combine parameters describing the overall responsiveness of the patient to "unconscious" stimulations. This may be defined by means of the hemodynamic, motor, and endocrine stability. A promising basis for searching a multi-parameter monitoring method for sub-cortical activity can thus possibly be found from the subtle features in the common vital signs, the heart rate, the respiration rate, the blood circulation, and the blood pressure.

The sub-cortical integrity of the afferent input, ANS evaluations, and efferent autonomic output is best researched in unconscious subjects with noxious stimulations and their responses, as these are mainly processed and modulated in the brainstem and spinal levels. The responses can also be modulated (attenuated) by analgesic or antinociceptive drugs, which influence the pain pathways at the sub-cortical levels. A successful monitoring method shall thus demonstrate a clear relationship and correlation between both the effect of the analgesics on the suppression of the nociceptive responses and the intensity of the noxious stimulations on the strength or amount of the responses in the parameters.

The need for reliable monitoring of the adequacy of anesthesia is based on the quality of patient care and on economy related aspects. Balanced anesthesia reduces surgical stress and there is firm evidence that adequate analgesia decreases postoperative morbidity. Awareness during surgery with insufficient analgesia may lead to a post-traumatic stress disorder. Prolonged surgical stress sensitizes the central pain pathways, which post-operatively increases patient pain and secretion of stress hormones. Low quality pre- and intra-operative analgesia makes it difficult to select the optimal pain management strategy later on. More specifically, it may cause exposure to unwanted side effects during the recovery from the surgery. Too light an anesthesia with insufficient hypnosis causes traumatic experiences both for the patient and for the anesthesia personnel. From economical point of view, too deep an anesthesia may cause increased perioperative costs through extra use of drugs and time, and also extended time required for post-operative care. Too deep a sedation may also cause complications and prolong the usage time of expensive facilities, such as the intensive care theater.

U.S. Pat. No. 6,801,803 discloses a method and device for ascertaining the cerebral state of a patient. In this disclosure, a measure derived from EMG signal data enhances and confirms the determination of the hypnotic state made using EEG signal data. As the EMG data may be computed more frequently than the EEG data, this renders ascertaining changes in the hypnotic state of the patient more rapid. In this method, the (facial) EMG thus alone reflects the suppression of the nociceptive pathways. State entropy (SE), which is calculated in the low frequency band up to 32 Hz, is dominated by the cortical EEG activity, while response entropy (RE), which also includes the high frequencies, represents both the cortical and muscle activity. The difference RE-SE is, therefore, a measure of the (f)EMG power, which will increase at nociception and which, therefore, may be a good measure of the suppression of the pain pathways. However, the above-mentioned dependency on the medication of the patient may render the method unusable in certain situations. As the (facial) electromyography signal is affected by neuro-muscular blocking agents (NMBAs), which suppress signaling at the nerve-muscle junctions, the EMG component of the measurement may vanish and render the method unusable, if the medication of the patient includes neuro-muscular blocking agents. It shall also be emphasized that the difference RE-SE is not specific to the suppression of the pain pathways but also reflects the overall motoric activity following any arousals—that is emotional or normal sensory evoked arousals, too. For instance, when the patient is awake and not perceiving any pain or discomfort, the RE-SE difference is typically about 8-10 percent. At deep hypnosis it is obvious that only painful stimulations can cause RE to differ from SE, but it is difficult to tell at which level the transition to the only-nociception induced varying difference in the deep anesthesia takes place.

EP patent 0553162 proposes a method and apparatus for assessing the depth of anesthesia by using respiratory sinus arrhythmia (RSA) as a measure of the state of the brain. The document describes a method in which a parameter indicative of clustering of the heart beat pattern is determined from the ECG waveform relative to the beginning of each respiration cycle. This parameter is then compared with a reference value calculated using a test for randomness. The parameter is then compared with the reference value to derive a measurement of the depth of anesthesia. In particular with spontaneously breathing anesthetized patients, the clustering is proportional to the RSA, which decreases with deepening anesthesia. The heart rate changes influencing the clustering are primarily controlled by the parasympathetical branch of the ANS, and therefore, the depth of anesthesia is related to the parasympathetical activity. This, however, correlates poorly with sympathetical effects, i.e. with the pain and nociception, and therefore also poorly with the adequacy of analgesia. Furthermore, the clustering takes place differently in artificial over-pressure ventilation and in spontaneously breathing patients, as the heart rate always accelerates during the low pressure period of the respiration cycle and decelerates during the high pressure phase. The low pressure period occurs during the inspiration in case of spontaneously breathing patients and during the expiration in case of artificial ventilation. The proposed method works reasonably well for spontaneously breathing patients, who in addition have a large RSA, such as children, but often fails in connection with artificially ventilated older patients. Pain reduces RSA amplitudes, as does the deepening of anesthesia. As a result, a low value of clustering may suggest too deep an anesthesia, leading to a decrease in the level of hypnosis. This may, however, lead to a worse situation, as a result of which the patient may even wake up, especially if surgical stimulations are intense.

U.S. Pat. No. 6,120,443 also suggests a method based on a heart beat interval (ECG R-to-R peak interval, RRI) analysis to assess the depth of anesthesia. In this method, the degree of randomness of the heart beats is described by means of a fractal dimension of the series of the R-R Intervals, mathematically describing the correlation within the RRI series. High correlation is indicative of a low fractal dimension and of only very few (CNS) processes, which add irregularities in the RRI series. Low correlation and thus high randomness equals high fractal dimension, which implies that the anesthesia is light and that many processes influence the RRI series. The methods for calculating the fractal dimensions are computationally heavy. In addition, the suggested method suffers from the fact that the degree of both hypnosis and analgesia affect the fractal dimension. The orthogonality of the two measures corresponding to the cortical and subcortical activity is thus poor. Although the method was primarily suggested for measuring the hypnosis of the patient, it is probable that it will also correlate with the degree of the surgical stress, which increases hemodynamic instabilities and the fractal dimension of the RRI series. Using this method, it is thus difficult to tell, which type of a drug, an opioid or a hypnotic, is primarily needed, and whether the drug concentration should be added or reduced.

European patent application EP1273265 describes a simpler method for analyzing an RRI and a blood pressure (BP) time series. Furthermore, the method tries to make a clear distinction between the sympathetical and parasympathetical cardiovascular responses. The sympathetical responses correlating with the surgical stress increase the heart rate and blood pressure. The acceleration index of the heart rate and the index for the increase of the blood pressure are calculated using a filter, a kind of edge filter, which detects the increasing slopes in the values of RRI or BP, but neglects the decreasing values. The document suggests that these indices may be used as a measure of the adequacy of analgesia. However, the method lacks the specificity to noxious stimuli and detects also the variations caused by respiration and other increasing slopes resulting from normal sympathetical activation without noxious stimulation. For instance, when the patient is in light anesthesia, both the sympathetical and parasympathetical branch of the ANS is active and the indices show erroneously high values suggesting insufficient analgesia.

The above prior art technologies thus aim to describe the adequacy of anesthesia using a unidimensional concept for the depth of anesthesia. They do not account for separate hypnotic and analgesic components, which are orthogonal, i.e. as much independent of each other as possible, and specific to the hypnotic and analgesic medications given during anesthesia. Thus the prior art methods cannot not answer to the question, whether one should add or reduce the analgesics or hypnotics in order to restore a balanced anesthesia. All prior art technologies that are claimed to measure the adequacy of analgesia show a considerable dependence on the level of hypnosis and, consequently, at light anesthesia without any noxious stimulations show a value that is usually associated with poor analgesia. A further drawback of the prior art technologies is that the measurement values show a considerable inter-patient variability. This makes their interpretation, i.e. the interpretation of the adequacy of anesthesia, difficult.

International patent application WO 2004/034897 discloses a method and an apparatus for a plethysmographic based detection of nociception during anesthesia and sedation. In this method, predetermined pulse wave parameters are detected and compared with reference values obtained earlier by measuring the same parameters over a certain preceding time window. If a substantial change is detected in at least one pulse wave parameter, preferably in waveform amplitude, a change in another pulse wave parameter, preferably the position of the dicrotic notch, is determined. If both changes are substantial, the changes are displayed or recorded and interpreted as an indication of a nociceptive event. The method thus provides an indication of the presence of noxious stimulation. Since the method is based on detection of noxious events, i.e. short-lived changes in the signal, it cannot provide an indication of the basic level of antinociception. In other words, the relative balance between the analgesic drug effect and the level of noxious stimulation cannot be estimated or measured, which makes the method unsuitable for automatically controlling the delivery of analgesic drugs.

U.S. Patent application 2005/0010116 discloses a method and an apparatus for monitoring the condition of a patient under anesthesia or sedation In this method, a mathematical index for probability of patient comfort is calculated. The probability index is obtained as a combination of physiological parameters extracted from a plethysmographic waveform, an ECG waveform, and/or EMG power measured from patient forehead. Again, as in the above-referred WO application 2004/034897, the parameters in the probability index are referred to a certain reference value determined over a certain time window or at certain reference event. Since the index is only indicative of the probability of nociception, it cannot provide quantitative information of the level of nociception or of changes in the said level. Therefore, this algorithm is also unsuitable for automatically controlling the delivery of analgetics.

The present invention seeks to eliminate the above drawbacks by using a novel approach which enables the monitoring of the trend of the clinical state, such as the level of nociception, of a patient, and which also enables the verification of the current clinical state against a fixed scale.

SUMMARY OF THE INVENTION

The present invention seeks to provide a novel mechanism for monitoring the clinical state of a subject. The clinical state here refers to a physiological status of the subject, which is indicative of a need or effect of a treatment or intervention, where the term physiological relates to physiology, the science dealing with the functions of living matter and beings. The present invention further seeks to provide a mechanism that allows a quantitative measure of the current clinical state of a subject to be obtained continuously by means of a fixed scale which directly indicates the clinical state for various subjects and which is suitable in various measuring environments, thereby also making the mechanism suitable for automatic drug delivery systems.

In the present invention, a measure of the clinical state of a patient is generated directly based on a signal containing desired physiological information obtained from a patient by applying to said signal a normalization transform dependent on predetermined history data, such as previously measured values of the same signal. A normalization transform here refers to a transform that scales the input signal values to a predetermined output value range, whereby the signal values output from the normalization transform are within the predetermined value range.

In a typical application of the invention, in which the nociceptive state of a patient is determined, the physiological signal(s) or parameter(s) obtained from the patient is/are indicative of the cardiovascular function of the patient, especially of a pulsative component of a peripheral blood circulation of the patient, since changes in the pain state of the patient are reflected in the said signals or parameters. However, the physiological signal(s) or parameter(s) obtained from the patient may be any other signals or parameters indicative of the physiological feature pertaining to which the clinical state is to be determined. Furthermore, as the transform applied to the input signal is a normalization transform and typically dependent on subject-specific history data, the said signal may be transformed to an index signal that provides a fixed diagnostic scale whose readings are independent of the subject in question. In the basic embodiments of the invention, the output signal of the transform thus directly forms a subject-specific diagnostic index indicative of the clinical state of the subject.

Thus one aspect of the invention is providing a method for ascertaining the clinical state of a subject. The method includes the steps of acquiring a first measurement signal containing first type of physiological data obtained from a subject, applying a first normalization transform to the first measurement signal, the first normalization transform being dependent on predetermined history data, whereby a first normalized measurement signal having a predetermined value range is obtained, and forming a diagnostic index dependent on the first normalized measurement signal, the diagnostic index serving as a measure of the clinical state of the subject.

Another aspect of the invention is that of providing an apparatus for ascertaining the clinical state of a subject. The apparatus includes means for acquiring a first measurement signal containing first type of physiological data obtained from a subject, first transform means for applying a first normalization transform to the first measurement signal, the first normalization transform being dependent on predetermined history data, whereby the first transform means are configured to output a first normalized measurement signal having a predetermined value range, and indicator means for indicating the clinical state of the subject as an index dependent on the first normalized measurement signal.

In further embodiments of the invention, the specificity of the index may be improved by determining a combined index based on the output signal of the normalization transform and at least one further signal, each of which is based on a different physiological signal or parameter and subjected to a normalization transform.

The solution of the invention provides an uncomplicated method for monitoring the clinical state of a subject and for accomplishing a diagnostic scale, such as a nociception scale, on which a certain reading corresponds to the same level for all patients.

The ability to continuously obtain a quantitative measure of the current clinical state of a patient also brings along two advantages. First, the said measure serves as reliable input information for a drug delivery system allowing automatic control of drug delivery. Second, the amount of drug needed may be predicted based on the changes in the said measure.

A further aspect of the invention is that of providing a computer program product by means of which known measurement devices, such as pulse oximeters, may be upgraded to enable monitoring of the clinical state of the patient. The program product includes a first program code portion configured to retrieve physiological data obtained from a subject, a second program code portion configured to apply a first normalization transform to the physiological data, wherein the second program code portion is configured to output a first normalized measurement signal having a predetermined value range, and a third program code portion configured to indicate the clinical state of the subject as an index dependent on the first normalized measurement signal.

Still further aspects of the invention are those of providing a method and a system for controlling the clinical state of a patient. The control method includes the steps of acquiring a first measurement signal containing first type of physiological data obtained from a subject, applying a first normalization transform to the first measurement signal, the first normalization transform being dependent on predetermined history data, whereby a first normalized measurement signal having a predetermined value range is obtained, forming a diagnostic index dependent on the first normalized measurement signal, the diagnostic index serving as a measure of the clinical state of the subject, and controlling administration of at least one drug to the patient, the controlling step being performed based on the diagnostic index. The system in turn includes means for acquiring a first measurement signal containing first type of physiological data obtained from a subject, first transform means for applying a first normalization transform to the first measurement signal, the first normalization transform being dependent on predetermined history data, whereby the first transform means are configured to output a first normalized measurement signal having a predetermined value range, drug delivery means for administering at least one drug to the patient, and control means for controlling the drug delivery means based on an index dependent on the first normalized measurement signal.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 10 in the appended drawings, wherein.

DETAILED DESCRIPTION OF THE INVENTION

Below, the invention is described more closely by referring first to embodiments pertaining to the determination of the antinociceptive component of anesthesia in a patient.

Figure 1:
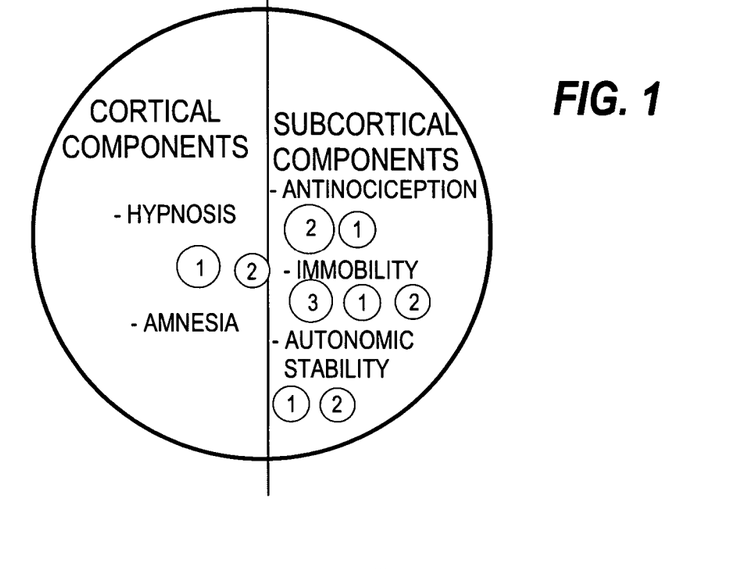
FIG. 1 illustrates the concept of the quality of anesthesia.

FIG. 1 illustrates the concept of the quality of anesthesia. According to the current comprehension, the quality of anesthesia includes five different components: hypnosis (i.e. unconsciousness), amnesia, antinociception, immobility, and the stability of the ANS. The first two components, the hypnosis and amnesia, are of cortical origin and are indicative of cortical activities and processes. The suppression of the cortical activity is obtained by drugs, which typically affect neural signaling globally in the brain. The drugs may activate the natural inhibitory GABA (gamma-aminobutyric acid) receptor system in the brains or prevent, by an unknown mechanism, neural signaling in the synapses between the neurons. For this reason, the drugs often also affect other parts than the cortex in the brain, thereby also suppressing subcortical activity and processes.

The other components in the anesthesia model, which are indicative of sub-cortex related activity in the patient, are much more specific and often relate to altering, modulating or blocking neural signaling at certain receptor or neurotransmitter level. These components can be affected selectively by different specific drugs. For instance, antinociception, i.e. the suppression of the neural transmission in the pain pathways, is achieved by opioid drugs, which affect the opioid/enkephalin receptors and activate the descending pathways, which block or modulate the nociceptive stimuli in the spinal cord. Furthermore, the NMBA drugs block the neural transmission in peripheral neuro-muscular junctions, which results in one kind of specific immobility of a patient. The stability of the ANS and the antinociception are closely related, since noxious stimulation in deep anesthesia causes hemodynamic and hormonal instability. The stability of the ANS is therefore also advanced by opioid drugs and by several other drugs, which may affect specifically the parasympathetical or sympathetical activities of the ANS.

FIG. 1 also shows the drugs associated with each component of the anesthesia model by showing numbered circles, in which number one refers to hypnotics, number two to opioids, and number three to NMBAs. Although many drugs may be involved in achieving an adequate level of the cortical and subcortical activity, the adequacy of anesthesia is often managed only by a gas anesthetic agent or other hypnotic agent, which dominantly (and globally) affects the cortical activity, and by an opioid, which selectively modulates the pain pathways at subcortical level, and by a NMBA drug, which induces immobility by blocking neuronal transmission in peripheral nerve-muscle junctions. The effects of the hypnotic agent may be monitored, for instance, by the above-described methods based on calculation of spectral entropy and the neuro-muscular blockade by an NMT (NeuroMuscular Transmission) measurement. The hypnotic and NMBA drugs can then be administered based on these measurements. The present invention provides a mechanism for obtaining a continuous measure of the amount of nociception in order to assess the antinociceptive component of anesthesia in a patient.

Pain-related responses may be monitored by detecting changes in the activity of the sympathetical branch of the ANS of the patient. For this purpose, sympathetical responses, i.e. short-lived signal changes which eventually return back to the base level of the signal, may be counted in a certain fixed time window, and pain may be detected if the rate of accepted responses exceeds a certain threshold value. To determine an appropriate threshold value for accepted response counts, the physiological signal involved may be normalized. Although this mechanism allows pain-related responses to be monitored, it does not provide quantitative information of the level of nociception or of changes in the said level.

Figure 2:
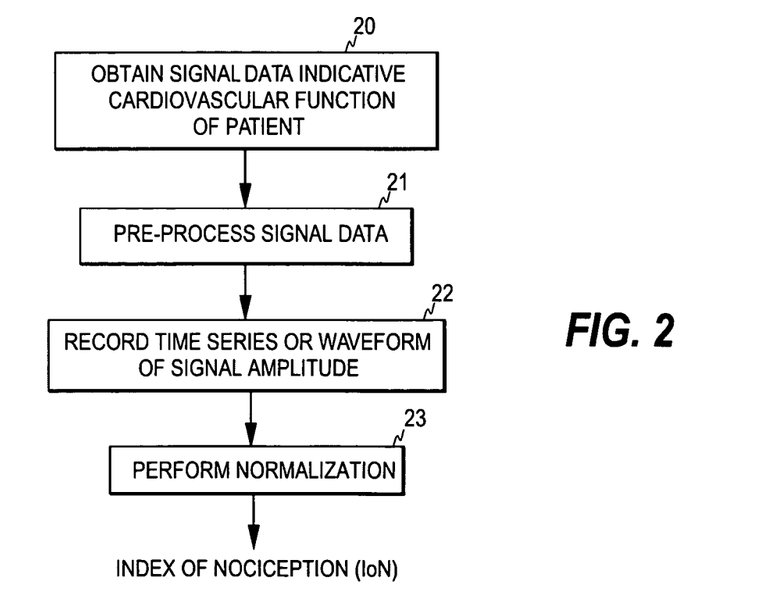
FIG. 2 is a flow diagram illustrating a first group of embodiments of the present invention.

The present invention offers a mechanism that allows a quantitative measure of the current clinical state of a subject to be obtained. FIG. 2 illustrates the basic embodiment of the present invention, in which an index of nociception, which is directly indicative of the amount of nociception, is formed by means of one normalized signal. In this basic embodiment, signal data indicative of the function of the cardiovascular system of the patient is first obtained from the patient (step 20), since changes in the level of nociception are reflected in such signals. Such signals include a plethysmographic signal, such as a photoplethysmographic (PPG) signal, a blood pressure (BP) signal, an ECG signal, or a Laser Doppler flow signal in peripheral tissues.

The cardiovascular system includes the heart, veins, arteries, and blood. Its main function is to transport oxygen and nutrients to all areas of the body and carry away carbon dioxide to the lungs and other wastes to the kidneys for excretion. The functions of the cardiovascular system induce a plurality of physiological signals that may be recorded to obtain information of the cardiovascular status of the subject. Such physiological signals include signals indicative of the peripheral blood circulation of the subject, such as a plethysmographic signal or a blood pressure signal. Blood pressure pulsation caused by the beating heart or air pressure variations in the lungs, for example, is mediated to the peripheries of the body through the vascular system. The tone of the vascular system regulates the conduction of the pulsation. Changes in the vascular tone form an independent source of pulsation detected in the peripheries of the body. Typical peripheral locations for the recording of the pulsation are finger tips and ear lobes. Therefore, most of the signals indicative of the function of the cardiovascular system, such as a PPG signal, a BP signal, or a Laser Doppler flow signal are also indicative of the pulsative component of the peripheral blood circulation.

The measurement of the signal waveform data may be implemented in a conventional manner, i.e. while the patient connected to a patient monitoring system, the signal waveform data is recorded and stored in a memory of a monitoring device. In order for the method to be quick enough, the measurement is such that new signal values are received frequently, for example at about 100 samples/sec.

The recorded waveform data may then be pre-processed at step 21 for filtering out some of the frequency components of the signal or for rejecting artifacts, for example. This step is not necessary, but may be performed to improve the quality of the signal data.

Next, the pulse amplitude of the waveform signal is extracted for each pulse beat at step 22, whereby a time series of the amplitude of the pulsative component of the peripheral blood circulation is obtained.

The said time series is then subjected to a normalization process in step 23. The normalization process here refers to a process that scales the input signal values to a predetermined output value range, such as 0 to 100.

The normalization process is further patient-adaptive, i.e. it adapts to the patient in question. In order to obtain the adaptation to the patient, the normalization transform is made dependent on time series data recorded previously for the same patient. For example, the normalization transform may be dependent on the mean and variance of the amplitude of the pulsative component, which are defined based on data measured earlier during a measuring period of a predetermined length, such as 5 minutes, or from a certain event to the present, such as since the beginning of the surgery.

A third characteristic feature of a typical normalization transform is that it emphasizes slow changes in the input signal. This is accomplished by making output values that correspond to the mean or center of the input value range relatively more sensitive to input value changes than the values in the tail regions. This mechanism enhances small changes or trends in the input values and damps large, jump-like responses in the input signal. The transform is thus especially suitable for detecting relative slow changes, i.e. trends, in the patient status, such as drug affected changes in the level of antinociception.

To sum up, a typical transform applied to the input signal at step 23 has three different properties:

- the transform is a normalization transform, i.e. it forces the input values to a predetermined output value range;
- the transform is patient-adaptive, i.e. as the transform is made dependent on signal data measured earlier from the current patient, it adapts to the patient; and
- the transform emphasizes slow changes in the input signal, which facilitates the monitoring of the trend in the clinical state.

A transform fulfilling the above criteria may be accomplished by various techniques, which include the use of a parameterized function transform or the use of a so-called histogram transform. The said two techniques are described in the following.

Figure 3:
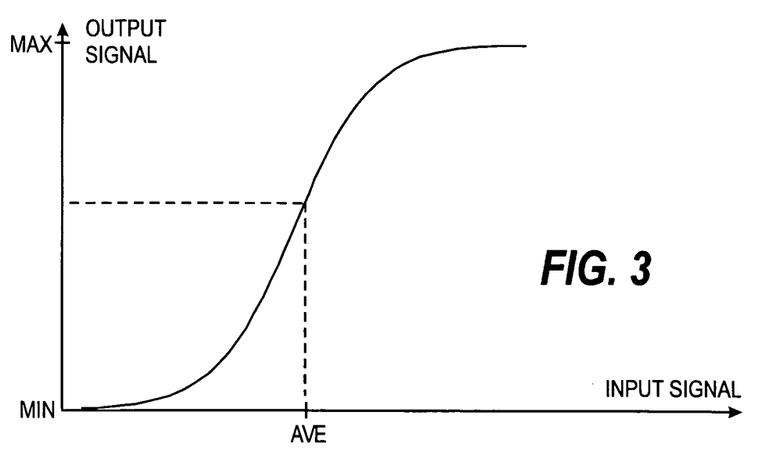
FIG. 3 illustrates typical input-output characteristics of the transform used in the embodiment of FIG. 2.

FIG. 3 illustrates typical input-output characteristics of the normalization transform. The curve of a typical function transform corresponds to a sigmoid function, i.e. the output value y depends on the input value x according to equation (1):

$$y = \frac{A}{1 + e^{-B*x}}, \quad (1)$$

where A and B are parameters. As discussed below, A is typically a positive constant determining the scale of the index values, while B may be a patient-specific parameter, which determines the distribution of the output index values within the scale from zero to A.

As can be seen from the figure, the transform forces the input signal to a predetermined output value range between a minimum value MIN and a maximum value MAX. For Eq. (1), MIN equals to 0, while MAX equals to A.

The adaptation to the patient may be accomplished by defining one or more patient-specific parameters and making the transform dependent on the said at least one parameter. For example, the mean<x> and standard deviation σ of the amplitude of the pulsative component may be determined prior to the surgery based on the time series data measured during measuring period of a predetermined length, such as 5 minutes. The transform may then be made dependent on the parameters determined. For example, parameter B may be set to a value equal to the inverse of the standard deviation, i.e. B=1/σ, and the input value x may be set to a value corresponding to the difference of the current input value $x_i$ and the mean value AVE, i.e. x=$x_i$-AVE, i.e. the input value may also be dependent on previous signal data.

An alternative function to Eq. (1) may be a cumulative distribution function of the Gaussian (normal) distribution function as depicted in Eq. (2):

$$f(X) = \frac{1}{\sigma\sqrt{2\pi}} \int_{-\infty}^{X} e^{-\frac{(x-<x>)^2}{2\sigma^2}} dx. \quad (2)$$

The above third feature, i.e. the emphasis of the slow changes may be accomplished by making the transform such that the slope of the transform curve is steepest around the input values that are most common, i.e. around the mean value AVE.

The output values of the transform are then used as a measure of the pain state of the patient. Thus, in this example the output value of the transform forms the index of nociception, which is indicative of the level of (anti)nociception in the patient. However, the index is not necessarily updated as frequently as a new output value is obtained, but the index may be calculated, for example, as an average over a certain number of output values output from the transform.

In the above-described manner, the time series of the amplitude of a signal indicative of the function of the cardiovascular system of the patient, such as a PPG signal, is transformed to a surrogate signal that has a predetermined value range and predetermined distribution characteristics for all patients. The transformation thus "forces" the values of the time series to a certain value range regardless of the incoming values, and a certain index value, such as 60, is indicative of the same amount of nociception for all patients.

As discussed above, a patient-adaptive normalization transform may be implemented by using a parameterized transform including at least one patient-specific parameter. Patient-specific parameter value(s) are measured prior to the actual measurement of the index of nociception, i.e. prior to the surgical procedure of a patient or during the surgical procedure but before the latest index value. The patient-specific values are then substituted for the said parameter(s) to obtain a patient-specific normalization transform. The patient-specific normalization transform is then used in step 23 to transform the incoming time series to the index of nociception.

Figure 4:
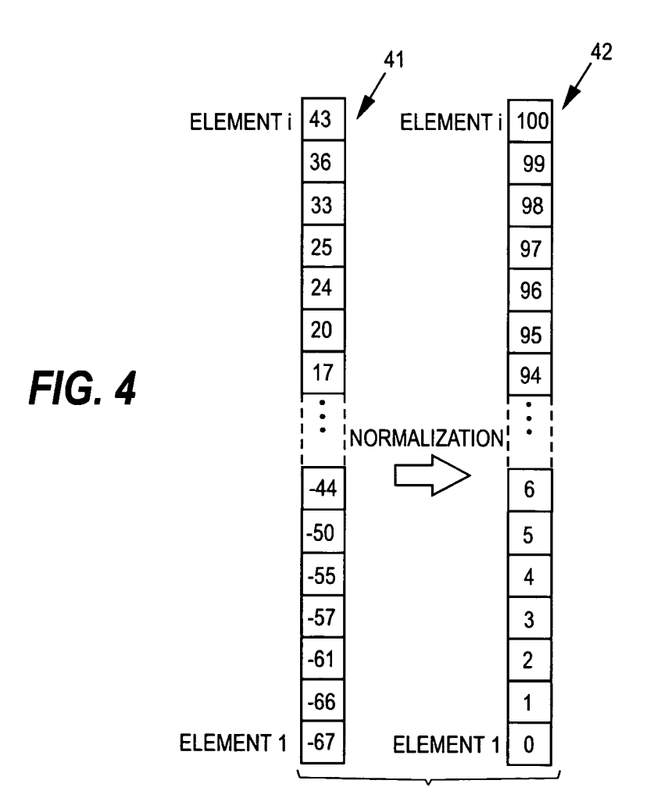
FIG. 4 illustrates the implementation of one embodiment of the normalization transform according to the invention.

Some or all of the above-described three basic properties of the transform may also be achieved by using a histogram transform in step 23. In a histogram transform, an input array 41 and an output array 42 are formed, as is shown in FIG. 4. The input array (buffer) comprises i input elements, also termed bins, storing, respectively, i input values sorted in ascending or descending order, while the output array (buffer) comprises fixed index values sorted in ascending or descending order and stored in i output elements. In the example of FIG. 4, the index values of the output buffer range from 0 to 100 corresponding to the total number of values in the input buffer, i.e. i=101. The values of the time series of the amplitude of the pulsative component, i.e. the values obtained from step 22, are thus forced to the value range of the output buffer. This may be implemented in three different ways depending on whether full adaptation, partial adaptation, or no adaptation to the incoming signal is utilized. These embodiments of the histogram transform are discussed briefly in the following.

In full adaptation, the latest signal values of the time series of the amplitude of the pulsative component are stored in the input array so that the value of each new data point obtained in the time series replaces the oldest value in the input array. When a new value is obtained from step 22, the oldest value in the input array is deleted, and the remaining values and the new value are sorted to form a new input array. The output value of the transform is then obtained by means of the output array as the index value that corresponds to the location of the new value in the input array. In this way, the level of the signal may change but the output values remain between the lowest and highest indices, i.e. in this example between 0 and 100. The time series obtained from the output array 32 may thus be such that the mean value is constant and the variability of the amplitude is limited to a certain range and certain distribution around the mean value. For instance, a Gaussian or even distribution with a desired mean value may be used for the values output from the transform.

Full adaptation may also be implemented by a parameterized transform. If a histogram transform is used, no patient-specific parameters are needed, since the sorting of previous signal data makes the histogram transform patient-adaptive. If a parameterized transform is used, no sorting of input data is needed.

In case no adaptation to the incoming signal is used in the histogram transform, the input array remains the same regardless of the incoming signal values. The input array may be formed based on values measured from a large patient group, which yields a wider distribution of input values than what is typically obtained for one patient. Thus, instead of storing the latest i values of the same patient, the input array may store i fixed values representing the distribution of the values of the amplitude of the pulsative component among a (large) group of patients. When a new value is obtained in the incoming time series from step 22, the corresponding output value of the transformation is obtained in the above-described manner as the index value that corresponds to the location of the new value in the sorted input array. Although this embodiment of the histogram transform is not patient-adaptive, different input arrays may still be defined for different patient groups, such as children or adults, and different input arrays may further be defined for each patient group according to various other parameters, such as the type of the sensor used or the peripheral site of the sensor (ear, finger, toe).

Similar non-adaptive transforms may be implemented by means of the parameterized transform. In this case the transform includes one or more parameters, whose value(s) depend on the patient group in question, and possible also on other parameters, such as the sensor type or site.

Figure 5A:
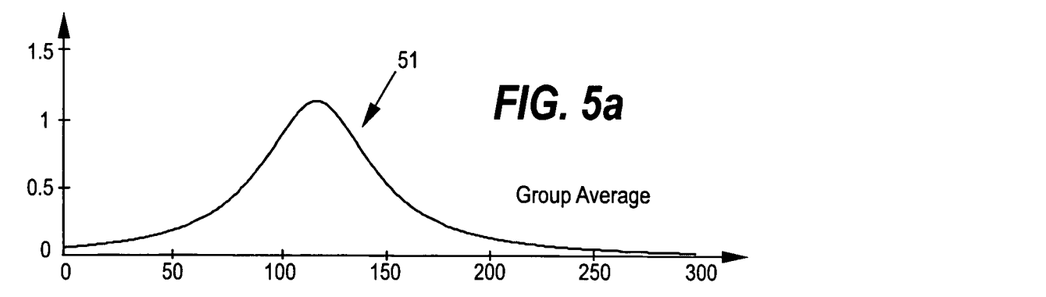
FIG. 5a to 5d illustrate one embodiment of the normalization process of the invention.
Figure 5B:
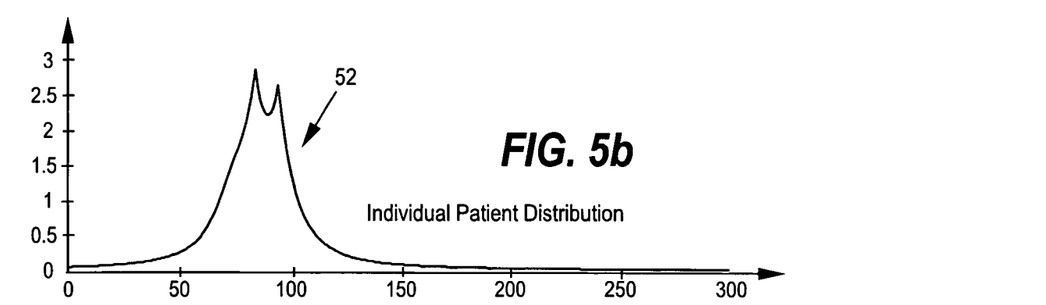
Figure 5C:
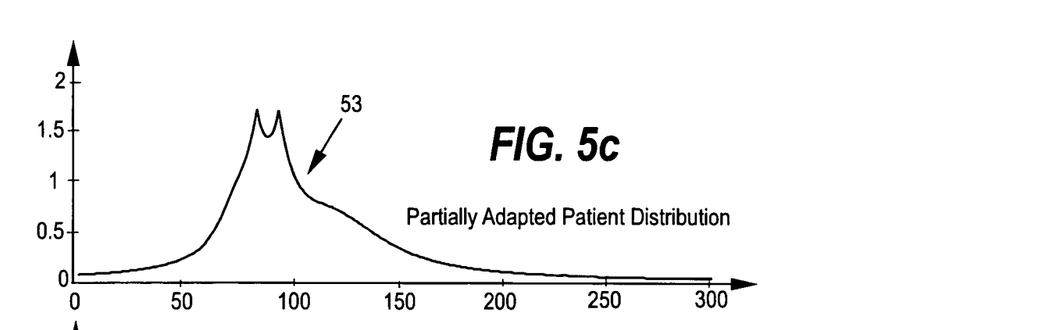
Figure 5D:
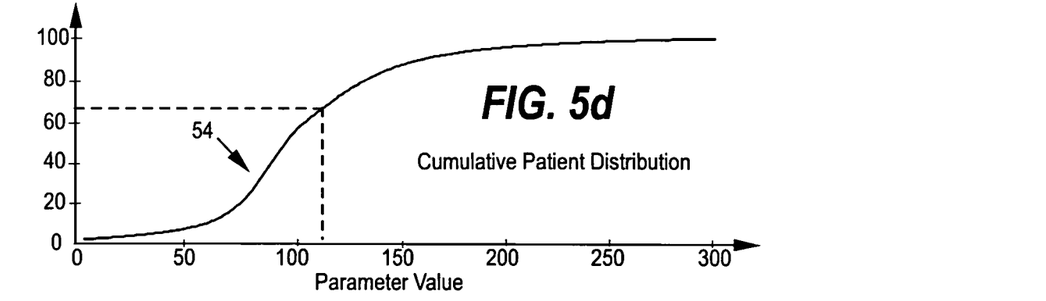

Partial adaptation to the incoming signal refers to the combination of the above two methods. An embodiment of the partial adaptation is illustrated in FIG. 5a to 5d. FIG. 5a illustrates a parameter distribution curve 51 for a large number of patients representing a certain patient group in general anesthesia. The size of the patient group may be very large representing about 1000 patients, for example. The range of the parameter values, in the figures from 0 to 300, is advantageously selected to be much wider than the actual range obtained during a surgery of an individual patient. During the surgery the same parameter, i.e. in this case the amplitude of the pulsative component of the blood circulation, is measured and a histogram distribution is created using the same parameter value bins as in the large population average. This distribution for the individual patient may contain a fixed number of values, e.g. 300, and the distribution may be updated using the full adaptation method described above. It is also possible that a cumulative distribution of the parameter values of the individual patient is collected and that the distribution counts so obtained are scaled down to a predetermined match in total counts to the patient group distribution. In such a case, the individual patient distribution may represent the parameter values since the beginning of the surgery till the current moment during surgery. An example of a normalized patient-specific distribution curve 52 obtained during a surgery is presented in FIG. 5b The normalized patient-specific distribution is then added in a predetermined proportion to the normalized patient group distribution, and an average total distribution curve 53 is formed, as shown in FIG. 5c. In this example, the two normalized distributions are weighted equally in the total distribution. For calculating the input parameter value array for the partially adapted histogram transform a cumulative sum of the average total distribution is then constructed as shown in FIG. 5d. If the histogram transform arrays are 101 element long, for example, the new values for the input bins of the histogram transform can be obtained by projecting the cumulative sum values 0, 1, 2, . . . , 100 of the Y-axis to the parameter value axis (X-axis), as is shown by dashed lines in FIG. 5d. The X-axis values obtained in this way form the input values of the input array for the histogram transform. The actual histogram transform is then executed without adaptation. In this embodiment, input values for the input array are thus obtained by adding a group distribution curve to the patient-specific distribution curve and then defining the input values for the input array by means of the cumulative distribution function of the summed distribution curve. Once being defined in the above-described manner, the input values of the input array remain fixed for a predetermined update interval, which can typically represent about 100 new individual parameter values.

The proportions of the adaptive and non-adaptive values in the combined input may vary. The same applies to the size of the steps between consecutive (fixed) values stored in the input or output arrays. For example, in the example presented in connection with FIG. 5a to 5d each consecutive input array bin contained one percent of the input values. However, the steps may also be such that a certain other percentage of values is within each step (i.e. in each bin), in which case the step may be smaller around one range of the input values and correspondingly larger around another range of the input values. The median value of the output signal, i.e. the center index of the output array, may be transformed to a desired output value, such as 50. The distribution of the output values may be specified according to the needs of the application.

As the adaptation to the patient is a preferred property for the normalization transform in the embodiments of FIG. 2, fully or partially adaptive normalization transforms are the preferred embodiments in step 23 of FIG. 2. As discussed above, in case of a partially adaptive transform, the normalization transform to be used at each time may depend on the patient, i.e. to which patient group the patient belongs, on the sensor used, and/or on the location of the sensor (finger or ear).

A generalized form of a partial patient adaptive histogram transformation may thus be presented as follows: H(patient adaptive transformation)=A*H1(large patient population)+B*H2(history data since the beginning of the surgery)+C*H3 (history data over the last M minutes), in which the first reference histogram H1 is for a large population group of similar patients (adults, children, infants, etc.) or for a particular type of sensor or equipment (PPG finger sensor, PPG ear sensor, etc.), the second reference histogram H2 is for the parameter values recorded since the beginning of surgery or anesthesia (long history data), and the third reference histogram H3 is for the parameter values recorded over the last M minutes, such as 5 minutes (short history data). The multiplying factors (A, B, and C, where A+B+C=1) are the relative weights of the separately normalized histogram distributions. The principal reason for the usage of a patient population histogram is that it contains the widest distribution of the parameter values, and thereby represents the allowable parameter range of the input values. The history data since the beginning of the anesthesia or surgery substantially sets each patient to the same norm. The histogram pertaining to the last M minutes allows a fast adaptation to trend-like parameter changes within one patient and thereby sets each phase of the surgery to a same equivalent norm, regardless of the absolute average value of the parameter in the time window of M minutes.

Partial adaptation may also be implemented by a parameterized transform. In this case, the transform includes both patient-specific and group-specific parameters in a fashion similar to the above histogram transformation. The parameters may be defined in various ways. For instance, the mean parameter in the function transform may be determined as a weighted mean of the mean values of the parameter in a large patient group data, in the long history data, and in the short history data of M minutes, while the variance parameter in the function transform may be determined as a weighted sum of the variances obtained from the two groups of history data.

In the basic embodiments of FIG. 2, the output signal of the normalization transform thus directly indicates the level of the antinociceptive component of anesthesia in the patient. In this context, the said output signal is termed the first normalized signal and the basic embodiments are said to form the first group of embodiments.

In further embodiments of the present invention, the specificity of the index of nociception to noxious stimulation and to analgesic drug concentration may be improved by producing a composite indication based on the first normalized signal and at least one other normalized signal made commensurable with the first normalized signal. This is discussed in the following.

Figure 6:
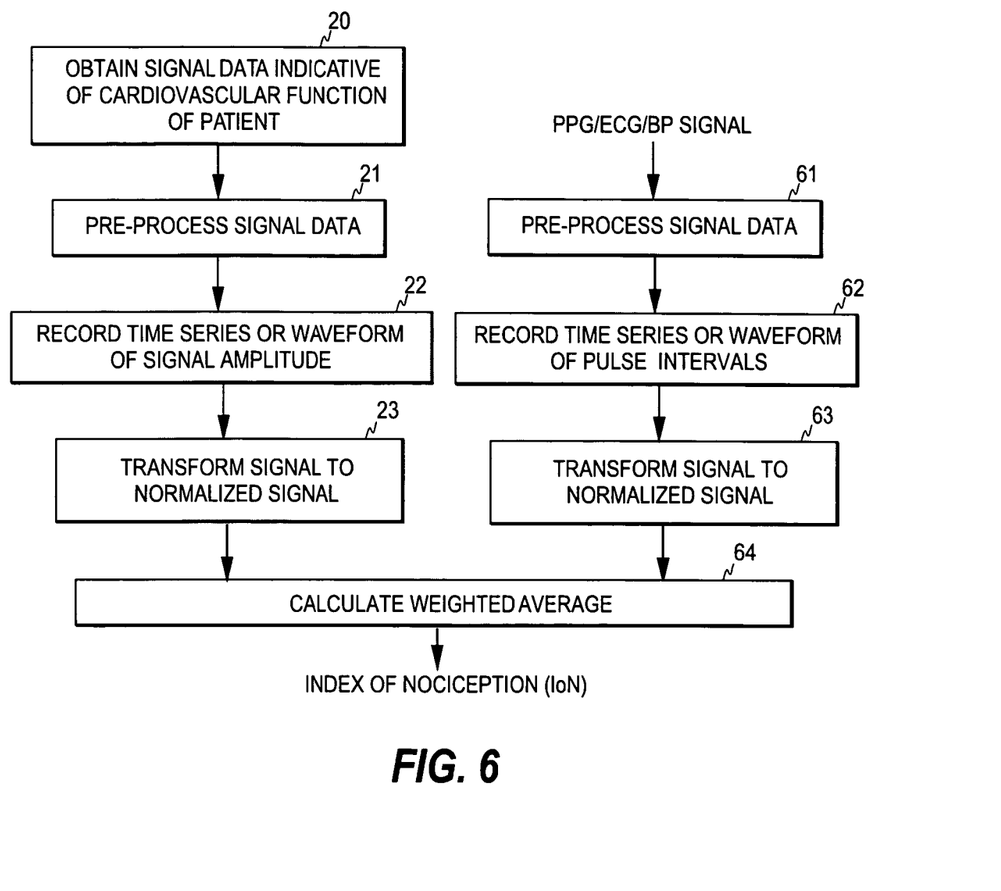
FIG. 6 illustrates a second group of embodiments of the invention.

In the second group of embodiments, which is illustrated in FIG. 6, the composite indication is formed based on two normalized signals. In these embodiments, the time domain is taken into account by producing the composite indication based on the first normalized signal and a normalized pulse interval, which is in this context termed the second normalized signal. The pulse interval here refers to the beat-to-beat interval of the physiological signal in question. The physiological signal may be a plethysmographic signal, an ECG signal, or a blood pressure signal. As either a plethysmographic signal or a blood pressure signal may be used to obtain the normalized pulsative component, the same signal data may be used to derive the time series of the pulse interval. Thus, in this case the signal may be supplied from step 21 directly to step 62, in which the time series of the pulse interval is generated. However, if the first and second normalized signals are based on different physiological signals, a pre-processing step 61 similar to step 21 may precede step 62.

The time series of the pulse interval is then subjected to a normalization transform at step 63 to obtain a time series of a normalized pulse interval.

In the second group of embodiments, the transform applied to the pulse interval is typically similar to the transform applied to the amplitude of the pulsative component in step 23. The transform is thus typically a fully or partially adaptive normalization transform, which may be implemented as a parameterized transform or as a histogram transform.

The normalized pulsative component and the normalized pulse interval are then combined at step 64 to form a composite indicator that serves as the index of nociception. This may be performed by calculating a weighted average of the two normalized values for each data point pair obtained from the two time series.

To give an example of preferred values of the two weights, the weighted average WA may be calculated for example as follows:

$$WA=-(0.43*RRI(norm)+0.57*PPGA(norm))+100,$$

where norm refers to normalized parameter values.

Figure 7:
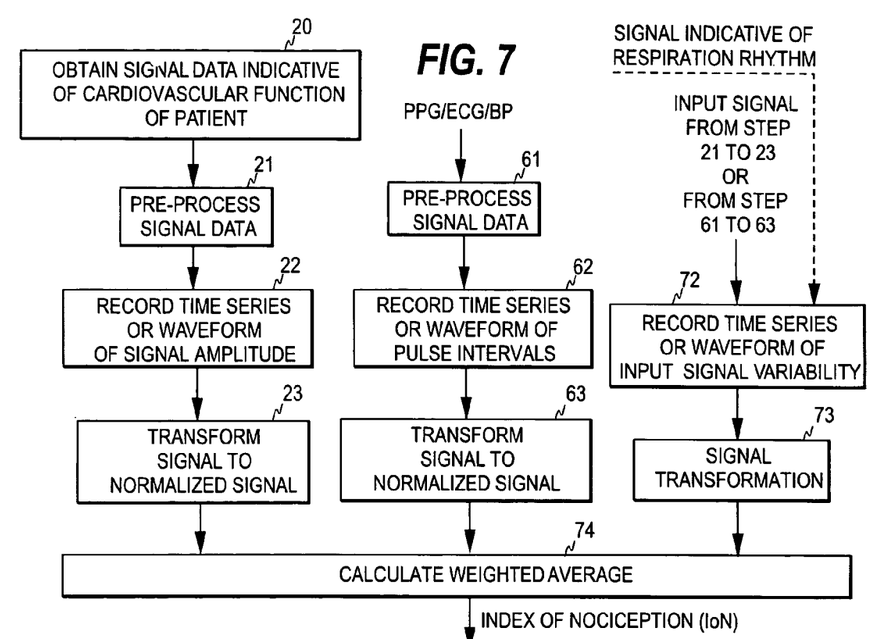
FIG. 7 illustrates a third group of embodiments of the invention.

In the third group of embodiments, the specificity of the index of nociception to noxious stimulation and to analgesic drug concentration may further be improved by adding a third normalized parameter to the group of normalized parameters whose weighted average forms the index of nociception. As is illustrated in FIG. 7, in one embodiment of the invention the third normalized parameter may be indicative of the variability of either the first or the second normalized signal or the corresponding non-normalized signal. The input signal to the input branch corresponding to the third normalized parameter may thus be supplied from any of steps 21 to 23 if the variability of the first signal is utilized or from any of steps 61 to 63 if the variability of the second signal is utilized. A time series or waveform of the third normalized parameter is then produced at step 72 by calculating, based on the input signal, a parameter which is indicative of the variability in the input signal. If the input signal is the pulse interval, the parameter calculated may be, for example, the ratio of the low frequency variability to the high frequency variability, i.e. the so-called sympatho-vagal balance, or a ratio similar to the sympatho-vagal balance. If the input signal is the pulsative component, the parameter calculated may be, for example, the power of respiratory variability. A signal indicative of the respiration rhythm of a patient may be utilized to calculate the parameter at step 72 in order to extract the frequency components needed for the calculation of the parameter indicative of variability. A desired signal component may be extracted by forming a time series phase-locked to the respiration rhythm of the patient. However, the signal indicative of the respiration rhythm of the patient does not necessarily have to carry phase information, but the desired signal component may also be separated by means of a filter controlled by the respiration rate of the patient. Different methods for using a signal indicative of the respiration rhythm of the patient for extracting desired signal components are described in Applicant's co-pending U.S. patent application Ser. No. 10/954,040, filed on Sep. 29, 2004.

A further signal transformation may be still needed for the third normalized parameter obtained from step 72 to make the said parameter commensurable with the first and second normalized parameters. This is then performed at step 73, if necessary. The transform performed at step 73 is typically non-adaptive, i.e. it is not dependent on previous signal data of the same patient. Instead, this normalization transform may depend on various other parameters, such as the type of the sensor and/or the location of the sensor. It may also represent an average distribution of the parameter values in a large patient population subjected to a certain clinical procedure, such as general anesthesia. Therefore, the normalization transform to be used may be selected at step 73 based on said other parameters or based on patient population.

The normalized pulsative component, the normalized pulse interval, and the normalized variability signal are then combined at step 74 to form a composite indicator that serves as the index of nociception. This may be performed by calculating a weighted average of the three normalized values obtained simultaneously in the three time series output respectively from the three transforms.

To give one example of preferred values of the three weights, the weighted average WA may be calculated for example as follows:

$$WA=-0.46*RRI(norm)+0.11*RRI(S\_V)-0.43*PPGA(norm)+89,$$

where RRI(norm) and PPGA(norm) are the normalized RRI and PPGA values, respectively, and RRI(S_V) is the normalized sympatho-vagal ratio determined for RRI.

Figure 8:
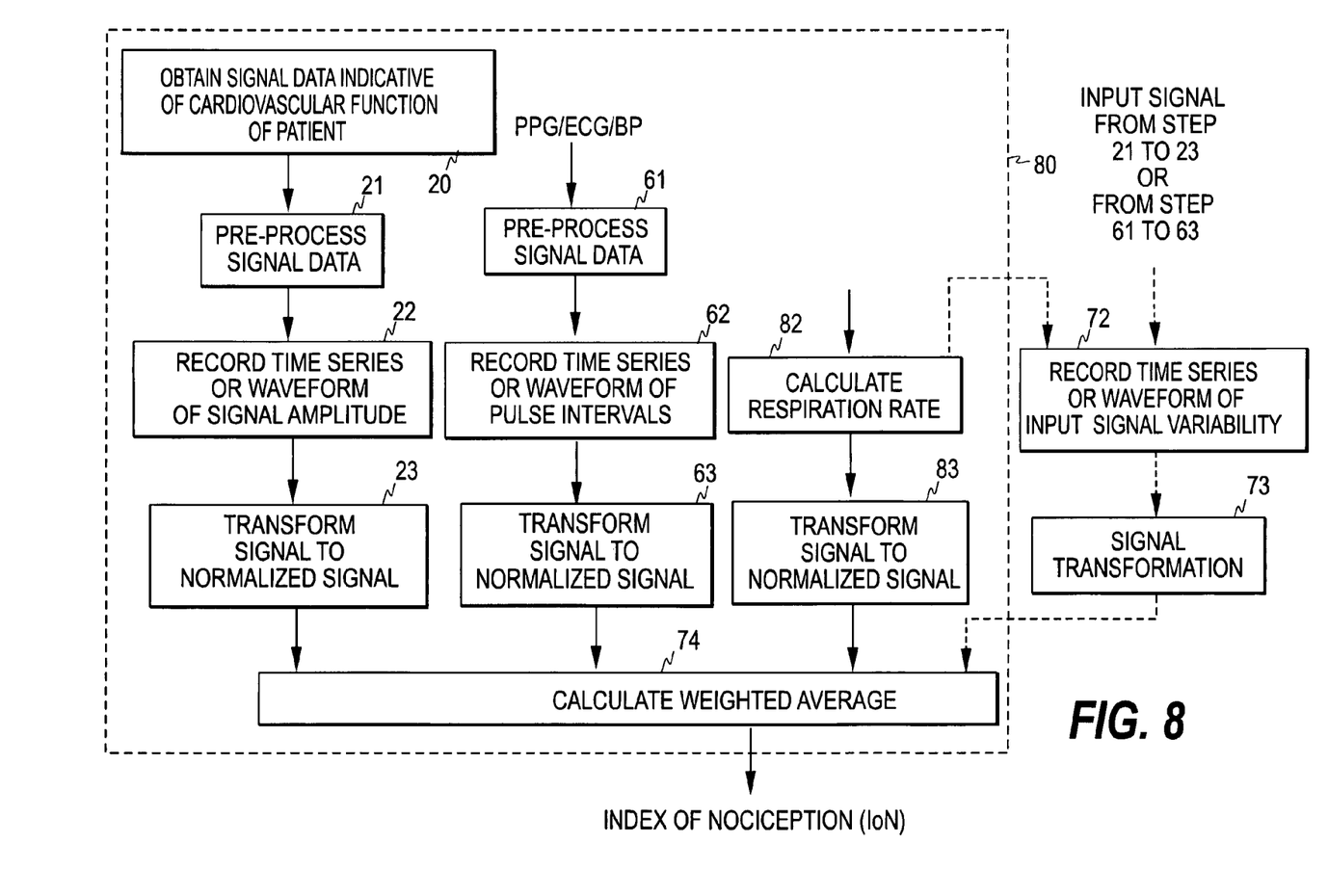
FIG. 8 illustrates further embodiments of the invention.

In another embodiment belonging to the third group of embodiments, the normalized respiration rate of the patient may be used instead of the normalized variability signal as the third normalized signal. FIG. 8 illustrates an embodiment 80, in which the normalized respiration rate of the patient is used as a third component of the weighted average. The use of the respiration rate is based on the fact that the respiration rate changes when the patient experiences pain. The respiration rate is derived at step 82 and the time series of the respiration rate is normalized at step 83. The respiration rate may be derived from an input signal, which may be a plethysmographic signal or an ECG signal. The input signal to step 82 may therefore be received from steps 20/21 or from step 61. The input signal may also be a respiration gas signal or a signal received from a particular respiration sensor attached to the patient. The normalization transform applied to the respiration rate is typically similar to those applied to the amplitude of the pulsative component and/or to the pulse interval at steps 23 and 63, respectively. Thus, in this embodiment the index of nociception is calculated as the weighted average of the normalized pulsative component, the normalized pulse interval, and the normalized respiration rate.

It is also possible to use more than three normalized signals for the determination of the index of nociception by adding new physiological signals, by deriving new normalized signals from the physiological signals already employed, and/or by using a combinatory embodiment. For example, the embodiments of FIGS. 7 and 8 may be combined, as is shown by the dashed arrows in FIG. 8. It is also possible to perform the normalization only after the calculation of the weighted average or to apply an additional normalization to the weighted average calculated based on normalized signals. Furthermore, different normalization transforms may be applied to different parameters and one parameter may be normalized in more than one way.

Above, the invention was described in connection with embodiments pertaining to the determination of a nociceptive or antinociceptive index. However, as human variability is a common problem relating to all physiological measurements and as the relative effect of different physiological features varies on a patient-to-patient basis, the invention may be utilized to improve specificity in connection with the determination of any diagnostic index indicative of a desired clinical state of the patient. For example, in the method described in the above-mentioned U.S. Pat. No. 6,801,803, in which a diagnostic index indicative of the cerebral state of the patient is calculated, the normalizing transform may be used in the above-described manner before the complexity measures forming the components of the diagnostic index are calculated. Similarly, normalization may be used to improve specificity in connection with the determination of any diagnostic index, which is determined based on one or more physiological parameters or signals indicative of the physiological state in question.

Figure 9:
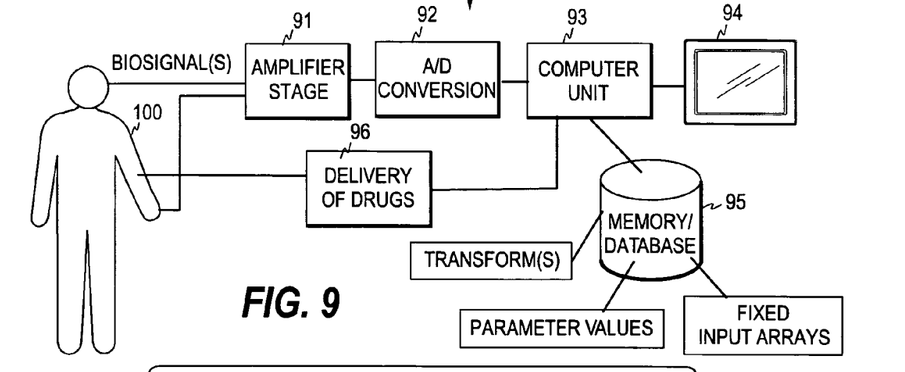
FIG. 9 illustrates one embodiment of a system according to the invention.

FIG. 9 illustrates one embodiment of the system or apparatus according to the invention. The physiological signal(s) obtained from one or more sensors attached to a patient 100 are supplied to an amplifier stage 91, which amplifies the signal(s) before they are sampled and converted into digitized format in an A/D converter 92. The digitized signals are supplied to a computer unit 93 which may comprise one or more processors.

The computer unit is provided with a memory or database 95 holding the digitized signal data obtained from the sensor(s). The computer unit may produce the time series needed, apply the normalization transform to each time series, and determine the diagnostic index based on the normalized signal value(s). For this purpose, the memory may store the transform(s) to be used, the patient-specific and/or group-specific parameter values needed for parameterized transforms, and/or the group-specific input arrays of the histogram transforms to be used. Although one computer unit or processor may perform the above steps, the processing of the data may also be distributed among different units/processors (servers) within a network, such as a hospital LAN (local area network). The apparatus of the invention may thus also be implemented as a distributed system.

The computer unit may display the results through at least one monitor 94 connected to the computer unit, and it may further supply the diagnostic index as input data to a device or system 96 delivering drugs to the patient, thereby enabling automatic control of the desired clinical state of the patient. For example, at least one analgesic may be delivered based on the index of nociception. The computer unit may act as a controlling entity controlling the administration of the drugs from the delivery system 96 to the patient. Alternatively, the computer unit may supply the diagnostic index to another computer unit or microprocessor (not shown), which then acts as the controlling entity controlling the drug delivery system 96. The said controlling entity is provided with the control data needed for the administration, such as the pharmacodynamic and pharmacokinetic properties of the drugs to be administered. The drug delivery system may comprise separate delivery units for one or more drugs to be administered, such as delivery unit for an analgesic drug and/or a delivery unit for a hypnotic drug.

Figure 10:
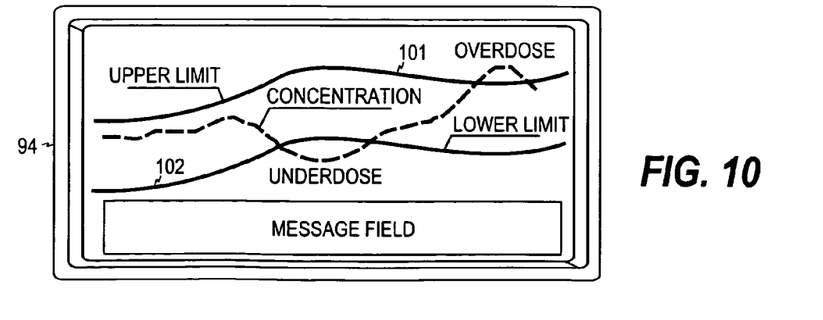
FIG. 10 illustrates an example of the use of the index of nociception as an analgesic infusion guide for an anesthesiologist.

The computer unit may also act as decision-support tool for the physician, such as an anesthesiologist, who then controls the drug delivery system based on the information provided by the computer unit. For example, the system of FIG. 9 may be provided with a monitor that displays the analgesic concentration during a surgery, for example, and also the recommended upper and lower limits for the said concentration. As is shown in FIG. 10, illustrating such a monitor, the recommended upper limit 101 and lower limit 102 of the analgesic concentration may further be controlled based on the index of nociception. If the index of nociception, shown as a dashed line, is too high (underdose), both limits shift up for a new infusion target and if the index is too low (overdose), both limits shift down. Thus, the recommendations concerning the use of the analgesic may be controlled based on the index of nociception and the controlled recommendations may be displayed to the anesthesiologist.

A conventional measurement device, such as a pulse oximeter, may also be upgraded to enable the device to determine the diagnostic index in the above-described manner based on the signal data that the device measures from the patient. Such an upgrade may be implemented by delivering to the measurement device a software module that enables the device to determine the diagnostic index in the above-described manner. The software module may be delivered, for example, on a data carrier, such as a CD or a memory card. The software module, which is provided with an interface to the memory storing the signal data measured by the measurement device, may apply any of the above-described normalization transforms to the signal data. It is also possible that a measurement device in which the determination of the diagnostic index is based on one or two normalized signals is upgraded by adding a further normalized signal to the group of normalized signals whose weighted average forms the diagnostic index.

Although the invention was described above with reference to the examples shown in the appended drawings, it is obvious that the invention is not limited to these, but may be modified by those skilled in the art without departing from the scope and spirit of the invention. For example, various predetermined dependencies between the diagnostic index and the normalized measurement signal(s) may be employed.

The invention claimed is:

1. A method for ascertaining a clinical state of a subject, the method comprising the steps of:
    acquiring a first measurement signal from the subject using one or more sensors, the first measurement signal containing desired physiological data reflecting the clinical state of the subject:
    utilizing a computer unit to apply a first normalization transform to the first measurement signal, the first normalization transform being subject specific and dependent on the distribution of previously acquired history data of the same type as the physiological data, wherein the previously acquired history data includes previous signal data of the first measurement signal from the subject, whereby a first normalized measurement signal having a predetermined value range is obtained; and
    utilizing the computer unit to form a diagnostic index which is dependent on the first normalized measurement signal, the diagnostic index serving as a measure of the clinical state of the subject.

2. A method according to claim 1, wherein the forming step includes forming the diagnostic index, in which the diagnostic index is proportional to the first normalized measurement signal.

3. A method according to claim 2, wherein the forming step includes employing the first normalized measurement signal directly as the measure of the clinical state of the subject.

4. A method according to claim 1, wherein the acquiring step is further defined as acquiring the first measurement signal containing a first type of physiological data; and the previously acquired history data includes both previous physiological data of the first type from the first measurement signal and physiological data of the first type obtained from a group of subjects.

5. A method according to claim 1, further comprising the steps of:
    determining at least one subject-specific value for at least one predetermined parameter of the first measurement signal; and
    substituting the at least one subject-specific value for at least one parameter in a predetermined parameterized transform to obtain the first normalization transform.

6. A method according to claim 1, wherein the applying step includes applying a histogram transform to the first measurement signal.

7. A method according to claim 6, wherein the applying step includes the sub-steps of:
    forming an input array for the first measurement signal, the input array including a predetermined number of input elements storing input values sorted in a desired order;
    creating an output array comprising output elements storing a predetermined number of index values sorted in a desired order;
    for an incoming signal value of the first measurement signal, determining the input element that corresponds to said incoming signal value in the input array; and
    transforming the incoming signal value to the index value stored in the output element corresponding to the determined input element.

8. A method according to claim 1, wherein the acquiring step includes a sub-step of deriving the first measurement signal from a first physiological signal indicative of the cardiovascular functioning of the subject.

9. A method according to claim 8, wherein the deriving sub-step includes deriving the first measurement signal from a first physiological signal comprising a plethysmographic signal measured from the subject.

10. A method according to claim 8, wherein the deriving sub-step includes deriving the first measurement signal from a first physiological signal comprising a blood pressure signal measured from the subject.

11. A method according to claim 8, wherein the forming step includes forming the diagnostic index, in which the diagnostic index serves as an index of nociception.

12. A method according to claim 11, further comprising a step of producing a second measurement signal containing signal data indicative of pulse intervals in a second physiological signal measured from the subject.

13. A method according to claim 12, further comprising a step of applying a second normalization transform to the second measurement signal, the second normalization transform being dependent on previously acquired history data, whereby a second normalized measurement signal having a predetermined value range is obtained.

14. A method according to claim 13, wherein the forming step includes calculating a weighted average of the first normalized measurement signal and the second normalized measurement signal.

15. A method according to claim 12, wherein the second physiological signal is indicative of the cardiovascular functioning of the subject.

16. A method according to claim 15, wherein the second physiological signal and said first physiological signal are the same.

17. A method according to claim 12, further comprising a step of producing a third measurement signal containing signal data indicative of variability in a third physiological signal obtained from the subject.

18. A method according to claim 17, further comprising a step of applying a third normalization transform to the third measurement signal, whereby a third normalized measurement signal having a predetermined value range is obtained.

19. A method according to claim 18, wherein the forming step includes calculating a weighted average of the first normalized measurement signal, the second normalized measurement signal, and the third normalized measurement signal.

20. A method according to claim 19, further comprising a step of selecting a temporally invariant transform as the third normalization transform.

21. A method according to claim 18, further comprising a step of producing a fourth measurement signal containing signal data indicative of the respiration rate of the subject.

22. A method according to claim 21, further comprising a step of applying a fourth normalization transform to the fourth measurement signal, whereby a fourth normalized measurement signal having a predetermined value range is obtained.

23. A method according to claim 22, wherein the forming step includes calculating a weighted average of the first, second, third and fourth normalized measurement signals.

24. A method according to claim 17, wherein the third physiological signal is indicative of the cardiovascular functioning of the subject.

25. A method according to claim 24, wherein the third physiological signal and said first physiological signal are the same.

26. A method according to claim 24, wherein the third physiological signal and said second physiological signal are the same.

27. A method according to claim 12, further comprising a step of producing a third measurement signal containing signal data indicative of the respiration rate of the subject.

28. A method according to claim 27, further comprising a step of applying a third normalization transform to the third measurement signal, whereby a third normalized measurement signal having a predetermined value range is obtained.

29. A method according to claim 28, wherein the forming step includes calculating a weighted average of the first normalized measurement signal, the second normalized measurement signal, and the third normalized measurement signal.

30. A method according to claim 11, further comprising a step of controlling administration of at least one analgesic drug to the patient, the controlling step being performed based on the index of nociception.

31. A method according to claim 8, wherein the deriving sub-step includes generating a time series indicative of the amplitude of the first physiological signal, the time series comprising the first measurement signal.

32. A method according to claim 1, further comprising a step of determining, based on the diagnostic index, at least one reference value serving as an instruction for administering a drug to the subject.

33. An apparatus for ascertaining a clinical state of a subject, the apparatus comprising:
    means for acquiring a first measurement signal from the subject using one or more sensors, the first measured signal containing desired physiological information data reflecting the clinical state of the subject;
    first transform means for applying a first normalization transform to the first measurement signal, the first normalization transform being subject specific and dependent on the distribution of previously acquired history data of the same type as the physiological data, wherein the previously acquired history data includes previous signal data of the first measurement signal from the subject, whereby the first transform means are configured to output a first normalized measurement signal having a predetermined value range; and
    indicator means for indicating the clinical state of the subject as an index which is dependent on the first normalized measurement signal.

34. An apparatus according to claim 33, wherein the index is proportional to the first normalized measurement signal.

35. An apparatus according to claim 33, wherein the first measurement signal contains a first type of physiological data and the previously acquired history data includes both previous physiological data of the first type from the first measurement signal and physiological data of the first type obtained from a group of subjects.

36. An apparatus according to claim 33, wherein the indicator means are configured to indicate the value of the first measurement signal as said index.

37. An apparatus according to claim 33, further comprising:
    measurement means for determining at least one subject-specific value for at least one predetermined parameter of the first measurement signal; and
    means for substituting the at least one subject-specific value for at least one parameter in a predetermined parameterized transform to obtain the first normalization transform.

38. An apparatus according to claim 33, wherein the first transform means are configured to apply a histogram transform to the first measurement signal.

39. An apparatus according to claim 38, wherein the first transform means are provided with
    an input array for the first measurement signal, the input array including a predetermined number of input elements storing input values; and
    an output array comprising output elements storing a predetermined number of index values sorted in a desired order.

40. An apparatus according to claim 39, wherein the first transform means are further provided with means for sorting the input values in a desired order.

41. An apparatus according to claim 33, wherein said means for acquiring the first measurement signal are configured to derive the first measurement signal from a first physiological signal indicative of the cardiovascular functioning of the subject.

42. An apparatus according to claim 41, wherein said index serves as an index of nociception.

43. An apparatus according to claim 42, further comprising control means for controlling administration of at least one analgesic drug to the patient based on the index of nociception.

44. An apparatus according to claim 41, further comprising means for producing a second measurement signal containing signal data indicative of pulse intervals in a second physiological signal obtained from the subject.

45. An apparatus according to claim 44, further comprising second transform means for applying a second normalization transform to the second measurement signal, the second normalization transform being dependent on previously acquired history data, whereby the second transform means are configured to output a second normalized measurement signal having a predetermined value range.

46. An apparatus according to claim 45, wherein the previously acquired history data includes previous signal data of said second measurement signal.

47. An apparatus according to claim 46, further comprising means for producing a third measurement signal containing signal data indicative of variability in a third physiological signal obtained from the subject.

48. An apparatus according to claim 47, further comprising third transform means for applying a third normalization transform to the third measurement signal, wherein the third transform means are configured to output a third normalized measurement signal having a predetermined value range.

49. An apparatus according to claim 48, further comprising second calculation means for calculating a weighted average of the first normalized measurement signal, the second normalized measurement signal, and the third normalized measurement signal.

50. An apparatus according to claim 49, wherein the indicator means are configured to indicate the weighted average as said index.

51. An apparatus according to claim 48, wherein the third transform means are configured to select a temporally invariant transform as the third normalization transform.

52. An apparatus according to claim 48, further comprising means for producing a fourth measurement signal containing signal data indicative of variability in a third physiological signal obtained from the subject; fourth transform means for applying a fourth normalization transform to the fourth measurement signal to output a fourth normalized measurement signal; and
    second calculation means for calculating a weighted average of the first, second, third, and fourth normalized measurement signals.

53. An apparatus according to claim 47, wherein at least two of the first, second, and third physiological signals are the same signal.

54. An apparatus according to claim 45, further comprising first calculation means for calculating a weighted average of the first normalized measurement signal and the second normalized measurement signal.

55. An apparatus according to claim 54, wherein the indicator means are configured to indicate the weighted average as said index.

56. An apparatus according to claim 45, further comprising means for producing a third measurement signal containing signal data indicative of the respiration rate of the subject.

57. An apparatus according to claim 56, further comprising third transform means for applying a third normalization transform to the third measurement signal, wherein the third transform means are configured to output a third normalized measurement signal having a predetermined value range.

58. An apparatus according to claim 57, further comprising second calculation means for calculating a weighted average of the first normalized measurement signal, the second normalized measurement signal, and the third normalized measurement signal.

59. An apparatus according to claim 57, further comprising means for producing a fourth measurement signal containing signal data indicative of variability in a third physiological signal obtained from the subject.

60. An apparatus according to claim 59, further comprising fourth transform means for applying a fourth normalization transform to the fourth measurement signal, wherein the fourth transform means are configured to output a fourth normalized measurement signal having a predetermined value range.

61. An apparatus for ascertaining a clinical state of a subject, the apparatus comprising:
   a measurement unit configured to acquire a first measurement signal from the subject, the first measurement signal containing desired physiological data reflecting the clinical state of the subject;
   a data processing unit configured to apply a first normalization transform to the first measurement signal, the first normalization transform being dependent on the distribution of previously acquired history data of the same type as the physiological data, wherein the previously acquired history data includes revious sinal data of the first measurement signal from the subject, wherein the data processing unit outputs a first normalized measurement signal having a predetermined value range; and
   a display unit configured to display the clinical state of the subject as a diagnostic index dependent on the first normalized measurement signal, wherein the diagnostic index is a measure of the clinical state of the subject.

62. An apparatus according to claim 61, wherein the predetermined history data includes both previous signal data of the first measurement signal and physiological data obtained from a group of subjects.

63. A method for controlling a clinical state of a subject, the method comprising the steps of
   acquiring a first measurement signal from the subject using one or more sensors, the first measurement signal containing physiological data reflecting the clinical state of the subject;
   utilizing a computer unit to apply a first normalization transform to the first measurement signal, the first normalization transform being dependent on the distribution of previously acquired history data of the same type as the physiological data, wherein the previously acquired history data includes previous signal data of the first measurement signal from the subject, whereby a first normalized measurement signal having a predetermined value range is obtained;
   utilizing the computer unit to form a diagnostic index which is dependent on the first normalized measurement signal, the diagnostic index serving as a measure of the clinical state of the subject; and
   controlling administration of at least one drug to the patient, the controlling step being performed based on the diagnostic index.

64. A method according to claim 63, wherein the forming step includes forming the diagnostic index, in which the diagnostic index serves as an index of nociception; and
   the controlling step includes controlling the administration of the at least one drug to the patient, wherein the at least one drug is an analgesic drug.

65. A method according to claim 64, wherein the forming step includes forming the diagnostic index, in which the diagnostic index is proportional to the first normalized measurement signal.

66. A system for controlling a clinical state of a subject, the system comprising:
   means for acquiring a first measurement signal from the subject using one or more sensors, the first measurement signal containing physiological data reflecting the clinical state of the subject:
   first transform means for applying a first normalization transform to the first measurement signal, the first normalization transform being subject specific and dependent on the distribution of previously acquired history data of the same type as the physiological data, wherein the previously acquired history data includes previous signal data of the first measurement signal from the subject, whereby the first transform means are configured to output a first normalized measurement signal having a predetermined value range;
   drug delivery means for administering at least one drug to the patient; and
   control means for controlling the drug delivery means based on an index which is dependent on the first normalized measurement signal, wherein the index is a measure of the clinical state of the subject.

67. A system according to claim 66, wherein the at least one drug is an analgesic drug.

* * * * *